United States Patent
Lin et al.

(10) Patent No.: US 10,786,443 B2
(45) Date of Patent: Sep. 29, 2020

(54) METHOD FOR PROTECTING SKIN BY USING ORCHID CALLUS EXTRACT

(71) Applicant: TCI CO., LTD, Taipei (TW)

(72) Inventors: Yung-Hsiang Lin, Taipei (TW); Cheng-Shing Li, Taipei (TW); Kai-Wen Kan, Taipei (TW); Ciao-Ting Chen, Taipei (TW); Fu-Chen Liu, Taipei (TW)

(73) Assignee: TCI CO., LTD., Taipei (TW)

( * ) Notice: Subject to any disclaimer, the term of this patent is extended or adjusted under 35 U.S.C. 154(b) by 63 days.

(21) Appl. No.: 15/945,635

(22) Filed: Apr. 4, 2018

(65) Prior Publication Data

US 2018/0289613 A1 Oct. 11, 2018

Related U.S. Application Data

(60) Provisional application No. 62/483,722, filed on Apr. 10, 2017.

(51) Int. Cl.
| | |
|---|---|
| *A61K 36/00* | (2006.01) |
| *A61K 8/9794* | (2017.01) |
| *A61K 36/898* | (2006.01) |
| *A61Q 19/00* | (2006.01) |
| *A61P 17/18* | (2006.01) |
| *A61P 17/00* | (2006.01) |
| *A61Q 19/08* | (2006.01) |

(52) U.S. Cl.
CPC .......... *A61K 8/9794* (2017.08); *A61K 36/898* (2013.01); *A61P 17/00* (2018.01); *A61P 17/18* (2018.01); *A61Q 19/00* (2013.01); *A61Q 19/08* (2013.01); *A61K 2236/33* (2013.01); *A61Q 19/007* (2013.01)

(58) Field of Classification Search
None
See application file for complete search history.

(56) References Cited

U.S. PATENT DOCUMENTS

| 8,637,488 B2 | 1/2014 | Sasaki et al. |
| 9,089,504 B2 | 7/2015 | Kang et al. |

FOREIGN PATENT DOCUMENTS

| CN | 101980695 B | | 5/2013 |
| CN | 106266587 A | * | 1/2017 |
| IN | 201500212 I4 | * | 7/2016 |
| KR | 10-0931768 B1 | | 12/2009 |
| TW | 201420127 A | * | 6/2014 |

OTHER PUBLICATIONS

Makpol, Suzana, et al., "Modulation of collagen synthesis and its gene expression in human skin fibroblasts by tocotrienol-rich fraction," *Arch. Med. Sci.*, 7, 5, pp. 889-895 (2011).
Uitto, Jouni, et al., "The complexity of elastic fiber biogenesis in the skin—a perspective to the clinical heterogeneity of cutis laxa," *Exp. Dermatol.*, 22(2), pp. 88-92 (Feb. 2013).
Sayo, Tetsuya, et al., "Hyaluronan Synthase 3 Regulates Hyaluronan Synthesis in Cultured Human Keratinocytes," *The Journal of Investigative Dermatology*, 118, pp. 43-48 (2002).
Sibilla, Sara, et al., "An Overview of the Beneficial Effects of Hydrolysed Collagen as a Nutraceutical on Skin Properties: Scientific Background and Clinical Studies," *The Open Nutraceuticals Journal*, 8, pp. 29-42 (2015).
Sinha, Santosh, "Anti-oxidant gene expression imbalance, aging and Down syndrome," *Life Sciences*, 76, pp. 1407-1426 (2005).
Iyama, Teruaki, et al., "DNA repair mechanisms in dividing and non-dividing cells," *DNA Repair* (Amst.), 12(8); pp. 620-636 (2013).

* cited by examiner

*Primary Examiner* — Michael Barker
(74) *Attorney, Agent, or Firm* — Christensen, Fonder, Dardi & Herbert PLLC

(57) ABSTRACT

A method for protecting skin is provided, wherein the method comprises administering to a subject in need an effective amount of an orchid callus extract, and the extract is a polar solvent extract of a callus of orchid leaves. The method is especially for moisturizing skin, increasing skin tenderness, increasing skin abundance, increasing skin elasticity, tightening skin, reducing skin textures, delaying skin aging, assisting in increasing content of collagen, repairing skin tissues, preventing skin lesions, and/or promoting wound healing.

10 Claims, 7 Drawing Sheets

METHOD FOR PROTECTING SKIN BY USING ORCHID CALLUS EXTRACT

CROSS REFERENCE TO RELATED APPLICATIONS

This application claims priority to U.S. Provisional Application Ser. No. 62/483,722 filed on Apr. 10, 2017, in the United States Patent and Trademark Office, the disclosures of which are incorporated herein in their entirety by reference.

FIELD OF THE INVENTION

The present invention relates to the uses of an orchid callus extract in protecting skin, particularly to the uses of an extract of a callus of orchid leaves in protecting skin. The protecting skin uses include moisturizing skin, increasing skin tenderness, increasing skin abundance, increasing skin elasticity, tightening skin, reducing skin textures, delaying skin aging, assisting in increasing content of collagen, repairing skin tissues, preventing skin lesions, and/or promoting wound healing.

BACKGROUND OF THE INVENTION

Skin, which is the largest tissue of human body as well as the first line of defense against foreign invasion and external environmental stimuli, plays an important role in water retention, warm retention and sensation. The exposure to ultraviolet (UV) rays, radiation, and the microbes and particulate matters in the environment may cause a decrease in the water content of skin, accelerate the occurrence of skin aging phenomena (e.g., thickening of skin keratin, desiccation and desquamation of skin, generation of fine lines and dark spots, skin sagging, and degradation and loss of proteins), and even destroy the DNA of skin cells that may cause cytotoxicity and cellular variation and lead to skin lesions.

Collagen and hyaluronic acid both are important materials in increasing the water content of skin, wherein collagen not only serves the function of retaining water but also imparts resiliency and elasticity to skin. Elastin in skin's dermis is capable of supporting the structure of skin cells. Therefore, if the contents of collagen, hyaluronic acid and elastin in the skin could be increased, the effects of increasing skin extensibility and elasticity, tightening skin and smoothing fine lines on skin could be achieved, thereby alleviating the skin depression and sagging.

Recently, people pay much more attention on the issues of skin care and prefer to use natural and safe materials in skin care. Therefore, there is still a need in the art for a skin care approach that uses natural and safe materials. Inventors of the present invention found that orchid callus extract is effective in promoting syntheses of collagen, elastin and hyaluronic acid and assisting in repairing DNA in skin cells, and thus, can be used for moisturizing skin, increasing skin tenderness, increasing skin abundance, increasing skin elasticity, tightening skin, reducing skin textures, delaying skin aging, assisting in increasing content of collagen, repairing skin tissues, preventing skin lesions, and/or promoting wound healing.

SUMMARY OF THE INVENTION

An objective of the present invention is to provide a use of an orchid callus extract in the manufacture of a composition, wherein the extract is a polar solvent extract of a callus of orchid leaves, and the composition is used for protecting skin. Preferably, the orchid is *Phalaenopsis amabilis*. Preferably, the polar solvent is selected from a group consisting of water, C1-C4 alcohols, and combinations thereof. Preferably, the composition is a care product composition, a food product composition, or a pharmaceutical composition.

Another objective of the present invention is to provide a composition, which is used for protecting skin. The composition comprises an effective amount of an orchid callus extract, wherein the extract is a polar solvent extract of a callus of orchid leaves. Preferably, the polar solvent is selected from a group consisting of water, C1-C4 alcohols, and combinations thereof. Preferably, the composition is a care product composition, a food product composition, or a pharmaceutical composition.

The care product composition provided in accordance with the present invention is used for at least one of moisturizing skin, increasing skin tenderness, increasing skin abundance, increasing skin elasticity, tightening skin, reducing skin textures, and delaying skin aging. Preferably, the care product composition is an essence, an emulsion, or a lotion.

The food product composition provided in accordance with the present invention is used for assisting in increasing content of collagen in skin. Particularly, the food product composition is used for assisting in increasing content of type I collagen in skin. Preferably, the food product composition is a beauty beverage.

The pharmaceutical composition provided in accordance with the present invention is used for at least one of repairing skin tissues, preventing skin lesions, and promoting wound healing. The pharmaceutical composition could be provided as a form for transdermal administration, oral administration, or subcutaneous injection.

Still another objective of the present invention is to provide a method for protecting skin, comprising administering to a subject in need an effective amount of an orchid callus extract. The method is for at least one of moisturizing skin, increasing skin tenderness, increasing skin abundance, increasing skin elasticity, tightening skin, reducing skin textures, delaying skin aging, assisting in increasing content of collagen, repairing skin tissues, preventing skin lesions, and promoting wound healing. The orchid callus extract could be administered to the subject in need as a form of the composition as described above.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIGS. 1 to 4 illustrate the effects of orchid callus extract of the present invention on increasing contents of collagen, elastin and hyaluronic acid in skin, wherein FIG. 1 shows the relative expression level (fold) of COL1A1 and COL1A2 genes (*$p<0.05$, $p<0.01$), FIG. 2 shows the relative expression level (fold) of ELN gene ($p<0.01$), FIG. 3 shows the relative expression level (fold) of HAS3 gene, and FIG. 4 shows the relative expression level (fold) of CAT and SOD2 genes (* $p<0.001$), and wherein the cells in control group were cultivated in a medium free of orchid callus extract for 24 hours, and those in the "Extract" group were cultivated in a medium being externally added with orchid callus extract for 24 hours; and FIGS. 5 to 7 illustrate the effects of orchid callus extract of the present invention on assisting in repairing damaged DNA in skin cells, wherein FIG. 5 shows the relative expression level (fold) of MSH2, MLH1 and MSH6 genes (the aforementioned three genes belong to mismatch repair (MMR) genes) ( $p<0.01$, * $p<0.001$), FIG. 6 shows the relative expression level (fold) of ERCC1 gene (the aforementioned gene belongs to nucleotide excision repair (NER) genes) ( $p<0.01$), and FIG. 7 shows the relative expression level (fold) of UNG, OGG1 and APE1 genes (the aforementioned three genes belong to base excision repair (BER) genes) ( $p<0.01$, * $p<0.001$).

DESCRIPTION OF THE PREFERRED EMBODIMENTS

Figure 1:
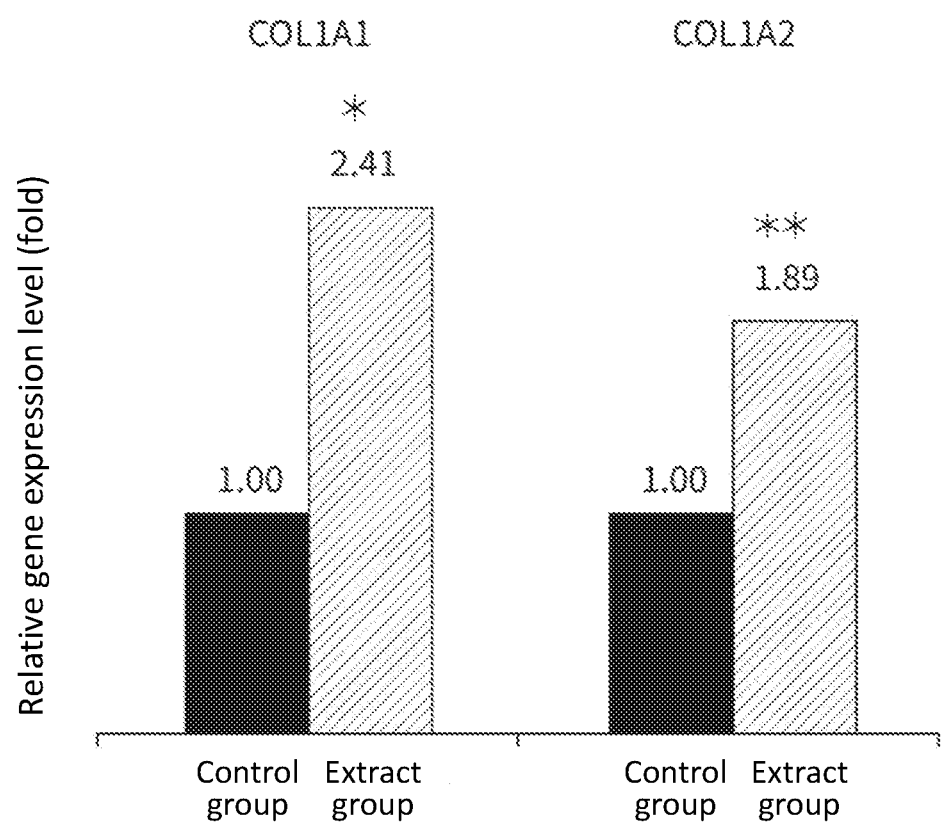

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an," "the," or the like recited in the specification of the present invention (especially in the claims) are intended to include both the singular and plural forms. The term "subject" recited in this specification refers to a mammalian, including human and non-human animals. Furthermore, unless otherwise indicated herein, the term "orchid callus" recited in this specification refers to a callus of orchid leaves.

Inventors of the present invention found that the features of calluses generated from the injured leaves of orchid plant are similar to those of the pluripotent stem cells of mammals, and the extract of orchid callus is effective in enhancing the antioxidant capability of skin cells, assisting in DNA repair of skin cells, and promoting syntheses of collagen, elastin and hyaluronic acid.

Therefore, the present invention relates to the uses of an orchid callus extract in protecting skin, including providing a composition comprising the orchid callus extract, a use of the orchid callus extract in the manufacture of a composition, and a method comprising using a composition comprising the orchid callus extract. The composition is used for protecting skin, especially used for moisturizing skin, increasing skin tenderness, increasing skin abundance, increasing skin elasticity, tightening skin, reducing skin textures, delaying skin aging, assisting in increasing content of collagen, repairing skin tissues, preventing skin lesions, and/or promoting wound healing. Particularly, the orchid callus is a callus of orchid leaves.

The orchid callus extract adopted in accordance with the present invention can be provided by extracting a callus of orchid leaves with a polar solvent, wherein the polar solvent can be a water, an alcohol (such as C1-C4 alcohols), or a combination thereof. The amount of the solvent used in the extraction step is not critical and is generally capable of evenly dispersing the materials to be extracted. For example, in the extraction step, the extraction solvent and orchid callus could be used at a weight ratio ranging from 100:1 to 300:1 (extraction solvent:orchid callus). Optionally, the extraction could be carried out accompanied with an ultrasonication to enhance the extraction efficiency. Preferably, a drying operation and/or a crushing operation could be conducted prior to the extraction.

In some embodiments of the present invention, orchid callus was freeze-dried prior to the extraction. For example, the freeze-dried orchid callus could be mixed with water at a weight ratio of 100:1 (water:freeze-dried orchid callus) to provide a mixture, and then, the mixture was subjected to an ultrasonic agitation at 70° C. for 45 minutes to accomplish the extraction. The orchid callus adopted in accordance with the present invention could be provided by the following steps:

I. Washing orchid plants with 6% sodium hypochlorite solution and then with sterile water, optionally, the aforementioned washing steps could be repeated;

II. Cutting the leaves of the washed orchid plants to create wounds on their surfaces to induce the callus generation (for 1 to 3 months); and III. Cultivating the callus(es) obtained from step II in a MS medium (Murashige and Skoog Basal Medium) at a temperature of 25° C. and a humidity of 50~60% (for 1 to 1.5 months).

The orchid callus extract adopted in accordance with the present invention could be an original form of the liquid extract directly obtained from the extraction of orchid callus, or a product obtained from carrying out one or more optional steps such as filtration, sterilization, concentration, and dilution on the liquid extract to facilitate the use of the liquid extract. For example, a concentrated liquid or a powder product, which is convenient for carry or storage, could be provided by subjecting the liquid extract to an operation such as concentrating-drying, spray-drying, or freeze-drying.

The composition provided in accordance with the present invention could be a care product composition, a food product composition, or a pharmaceutical composition, wherein the care product composition could be used for at least one of moisturizing skin, increasing skin tenderness, increasing skin abundance, increasing skin elasticity, tightening skin, reducing skin textures, and delaying skin aging. The care product composition in accordance with the present invention could be provided in any suitable form without specific limitations. For example, the care product composition could be an emulsion, a cream, a gel (such as a hydrogel), or solution (such as an essence, a lotion) for external use, but is not limited thereby.

The food product composition provided in accordance with the present invention is used for assisting in increasing content of collagen in skin, particularly in increasing content of type I collagen in skin, and could be provided in any suitable form without specific limitations. For example, the food product composition could be prepared as a form which is suitable for eating or drinking, such as a health food and a beauty beverage, but is not limited thereby.

Optionally, the care product composition, food product composition or pharmaceutical composition provided in accordance with the present invention could further comprise a suitable amount of additives, such as a flavoring agent, a toner, or a coloring agent for enhancing the palatability and the visual perception of the food product composition or pharmaceutical composition, and/or a buffer, a conservative, a preservative, an antibacterial agent, or an antifungal agent for improving the stability and storability of the care product composition, food product composition or pharmaceutical composition.

Depending on the desired purpose, the pharmaceutical composition in accordance with the present invention could be provided in any suitable form without specific limitations. For example, the pharmaceutical composition could be administered to a subject in need by an oral or parenteral (such as transdermal, or subcutaneous) route, but is not limited thereby. Depending on the form and purpose, suitable carriers can be chosen and used to provide the pharmaceutical composition, wherein the carriers include excipients, diluents, auxiliaries, stabilizers, absorbent retarders, disintegrating agent, hydrotropic agents, emulsifiers, antioxidants, adhesives, binders, tackifiers, dispersants, suspending agents, lubricants, hygroscopic agents, etc.

As a dosage form for oral administration, the pharmaceutical composition could comprise any pharmaceutically acceptable carriers that will not adversely affect the desired effects of the active ingredient (i.e., orchid callus extract). Examples of suitable carriers include, but is not limited to, water, saline, dextrose, glycerol, ethanol or its analogs, cellulose, starch, sugar bentonite, and combinations thereof. The pharmaceutical composition could be provided in any suitable form for oral administration, such as in a form of a tablet (e.g., dragee), a pill, a capsule, granules, a pulvis, a fluid extract, a solution, syrup, a suspension, a tincture, etc.

As a dosage form for transdermal administration, the pharmaceutical composition could be provided in a form of such as a patch, an emulsion, a cream, a gel (such as a hydrogel), a paste (such as a dispersing paste, an ointment), a spray, or a solution (such as a suspension) for external use, but is not limited thereby.

As for the form of injections or drips suitable for subcutaneous administration, the pharmaceutical composition could comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers. Alternatively, the pharmaceutical composition could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Depending on the need, age, body weight and health conditions of the subject as well as purpose, the composition provided in accordance with the present invention could be dosed at various administration frequencies, such as once a day, multiple times a day, once every few days, etc.

The present invention also provides a method for protecting skin, comprising administering to a subject in need an effective amount of an orchid callus extract. The orchid callus extract adopted in accordance with the method of the present invention could be administered to the subject in need as the form of a composition. The applied type, applied route, applied form, applied frequency and uses in related application of the composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

A. Preparation of Orchid Callus Extract

The *Phalaenopsis amabilis* plants were purchased from 232 Orchid Garden, Guoguang Flower Market (Taichung, Taiwan) and were subjected to the following operations to provide orchid callus(es):

I. Washing orchid plants with 6% sodium hypochlorite solution then with sterile water, optionally, the aforementioned washing steps could be repeated;
II. Cutting leaves of the washed orchid plants to create wounds on their surfaces to induce the callus generation (for 1 to 3 months); and
III. Cultivating the callus(es) obtained from step II in a MS medium (Murashige and Skoog Basal Medium, purchased from SIGMA company, product number: M5519) at a temperature of 25° C. and a humidity of 5060% (for 1 to 1.5 months).

The orchid calluses obtained from step III were subjected to the following operations to prepare an orchid callus extract:

(1) Freeze-drying the orchid calluses at −22° C. for 12 hours, then crushing the dried orchid calluses to provide an orchid callus powder;
(2) Mixing the orchid callus powder obtained from step (1) with water at a weight ratio of water:orchid callus powder=100:1 to provide a mixture, then subjecting the mixture to an ultrasonic agitation at 70° C. for 45 minutes;
(3) Filtrating the product of step (2) with a filter membrane to provide a filtrate;
(4) Heating the filtrate obtained from step (3) to 95° C. and maintaining at 95° C. for 20 minutes to sterilize;
(5) Cooling the product of step (4), then packing and keeping the product in cold storage for use in the following experiments; and
(6) Freeze-drying the product of step (5) to provide a dry matter (i.e., the orchid callus extract adopted in accordance with the present invention).

B. Cellular Treatment

Human skin fibroblasts (CCD-966SK; purchased from ATCC) were cultivated in a MEM medium (Minimum Essential Medium; purchased from Gibco company, product number: 61100-061) for 24 hours. Thereafter, the human skin fibroblasts were divided into two groups and independently subjected to the following treatments:

1. Control group: cells were cultivated in a MEM medium for 24 hours (i.e., the cells were cultivated in a medium free of orchid callus extract).
2. "Extract" group: cells were cultivated in a MEM medium being externally added with 1 wt % orchid callus extract (as dry matter) obtained from step (6) of [Preparation Example A] for 24 hours.

C. Preparation of cDNA

Cells of each group provided by [Preparation Example B] were harvested and subjected to an RNA extraction with a RNA extraction kit (purchased from GENEmark company). Then, the RNA was transcribed into cDNA with a reverse transcriptase. The cDNA is for use in the following gene expression examination.

Example 1: Effects of Orchid Callus Extract on Increasing Content of Collagen, Elastin and Hyaluronic Acid in Skin It is known that an increment in the expression level of genes such as COL1A1, COL1A2, ELN, and HAS3 of skin cells is helpful for promoting the syntheses of collagen, elastin and hyaluronic acid, and this can be noted from such as "Modulation of collagen synthesis and its gene expression in human skin fibroblasts by tocotrienol-rich fraction. *Arch Med Sci.* 7, 5: 889-895 (2011)," "The complexity if elastic fiber biogenesis in the skin—a perspective to the clinical heterogeneity of cutis laxa. *Exp Dermatol.* 22(2): 88-92 (2013)", "Hyaluronan Synthase 3 Regulates Hyaluronan Synthesis in Cultured Human Keratinocytes. *The Journal of Investigative Dermatology* 118: 43-48 (2002)", and "An overview of the Beneficial Effects of Hydrolysed Collagen as a Nutraceutical on Skin Properties: Scientific Background and Clinical Studies. *The Open Nutraceuticals Journal.* 8: 29-42 (2015), which are entirely incorporated hereinto by reference. To confirm effects of the orchid callus extract of the present invention on increasing contents of collagen, elastin and hyaluronic acid, the cDNA provided by [Preparation Example C] was subjected to a quantitative polymerase chain reaction (qPCR) by a ABI Step One Plus system and a KAPA SYBR FAST qPCR kit to determine the expression levels of COL1A1, COL1A2, ELN and HAS3 genes in the cells of each group. Then, the data thus obtained was analyzed by Student's t-test, and the result of control group was used as a basis (i.e., the gene expression level of control group was set as 1-fold) to calculate the relative gene expression level of "Extract" group. The results are shown in FIGS. 1 to 3.

Figure 2:
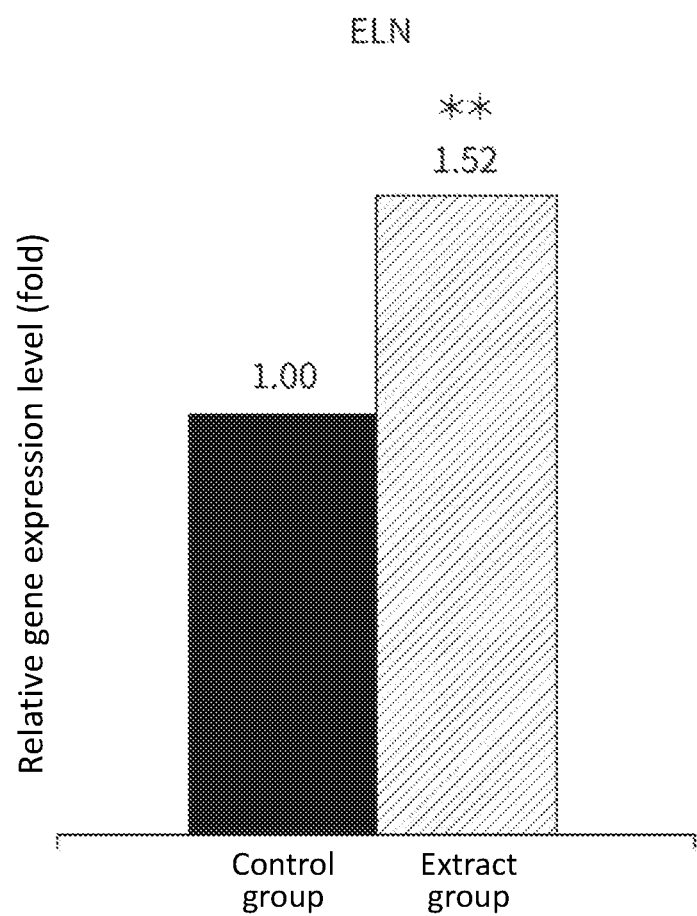
Figure 3:
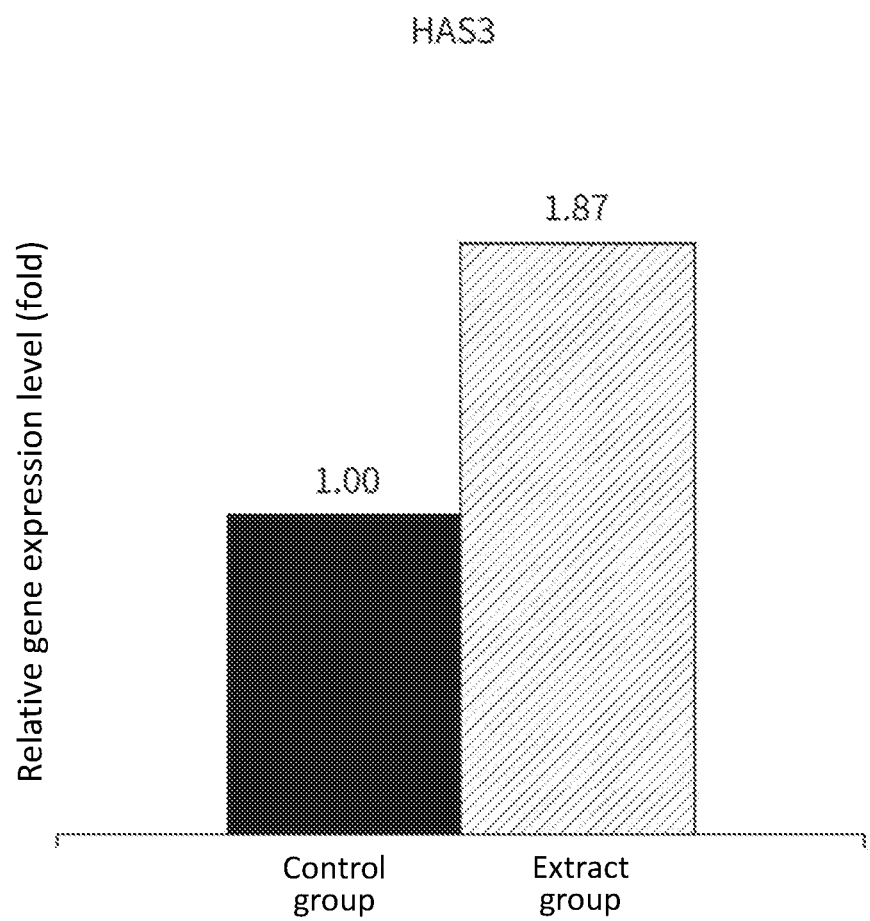

As shown in FIGS. 1 to 3, in comparison with the control group, the expression levels of COL1A1, COL1A2, ELN and HAS3 genes of "Extract" group were all significantly increased. The results indicate that orchid callus extract of the present invention can indeed increase the expression levels of COL1A1, COL1A2, ELN and HAS3 genes of skin cells, and thus, is effective in promoting syntheses and secretions of collagen, elastin and hyaluronic acid, thereby achieving the effects of moisturizing skin, increasing skin tenderness, increasing skin abundance, increasing skin elasticity, tightening skin, reducing skin textures, delaying skin aging, assisting in increasing content of collagen, and/or promoting wound healing.

Example 2: Effects of Orchid Callus Extract on Enhancing Antioxidant Capability of Skin It is known that an increment in the expression level of genes such as CAT and SOD2 of skin cells is helpful for enhancing the antioxidant capability of skin cells, and this can be noted from such as "Anti-oxidant gene expression imbalance, aging and Down syndrome. *Life Sciences*. 76: 1407-1426 (2005)," which is entirely incorporated hereinto by reference. To confirm the antioxidant capability of orchid callus extract, the cDNA provided by [Preparation Example C] was subjected to a quantitative polymerase chain reaction (qPCR) by a ABI Step One Plus system and a KAPA SYBR FAST qPCR kit to determine the expression levels of CAT and SOD2 genes in the cells of each group. Then, the data thus obtained was analyzed by Student's t-test, and the result of control group was used as a basis (i.e., the gene expression level of control group was set as 1-fold) to calculate the relative gene expression level of "Extract" group. The results are shown in FIG. 4.

Figure 4:
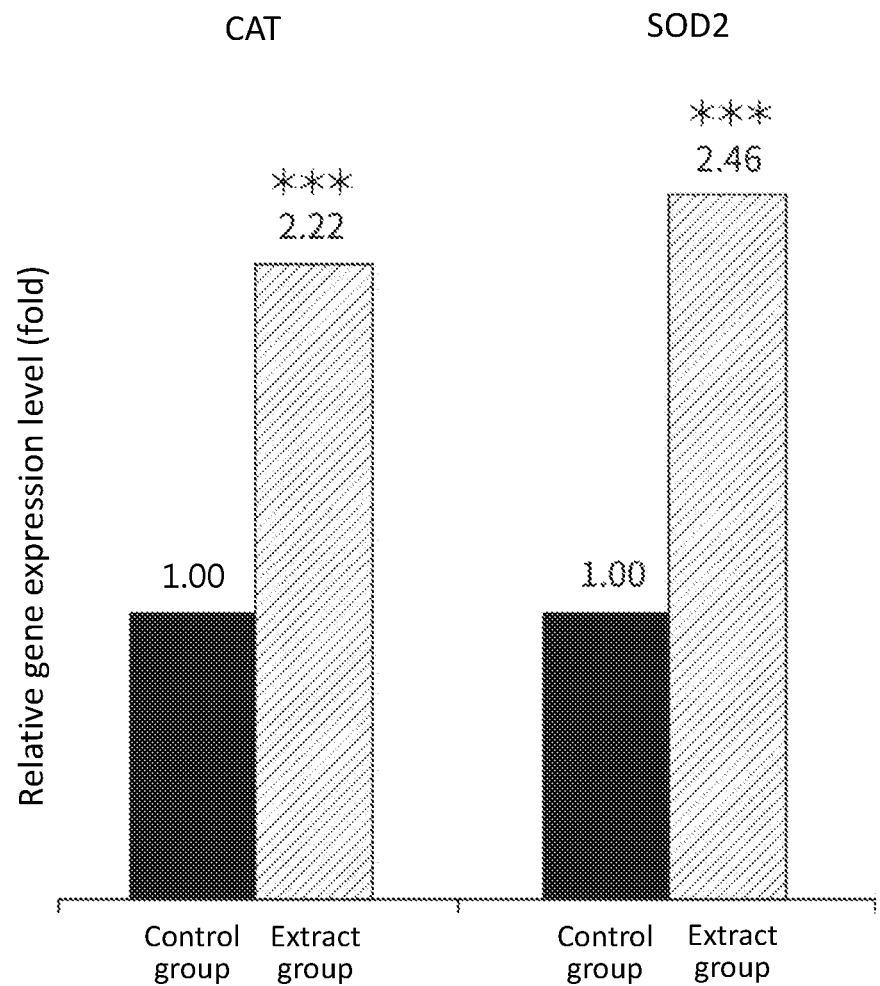

As shown in FIG. 4, in comparison with the control group, the expression levels of CAT and SOD2 genes of "Extract" group were all significantly increased. The results indicate that orchid callus extract of the present invention can indeed increase the expression levels of antioxidant genes of skin cells, and thus, is effective in enhancing the capability of skin cells to against the peroxide injuries, thereby achieving the effects of delaying skin aging, repairing skin tissues, and/or preventing skin lesions.

Example 3: Effects of Orchid Callus Extract on Assisting in Repairing Damaged DNA in Skin Cells It is known that the DNA repair mechanisms such as mismatch repair (MMR), nucleotide excision repair (NER), and base excision repair (BER) in the organism can prevent the DNA damage caused by mutation or breaks. Therefore, an increment in the expression levels of MMR-, NER- and BER-related genes of skin cells is helpful for repairing damaged DNA in skin cells, and this can be noted from such as "DNA repair mechanisms in dividing and non-dividing cells. *DNA repair (Amst)*. 12(8): 620-636 (2013)," which is entirely incorporated hereinto by reference. To confirm effects of the orchid callus extract of the present invention can assist in repairing damaged DNA in skin cells, the cDNA provided by [Preparation Example C] was subjected to a quantitative polymerase chain reaction (qPCR) by a ABI Step One Plus system and a KAPA SYBR FAST qPCR kit to determine the expression levels of MMR-related genes (including MSH2, MLH1 and MSH6), NER-related genes (including ERCC1), and BER-related genes (including UNG, OGG1 and APE1) in the cells of each group. Then, the data thus obtained was analyzed by Student's t-test, and the result of control group was used as a basis (i.e., the gene expression level of control group was set as 1-fold) to calculate the relative gene expression level of "Extract" group. The results are shown in FIGS. 5 to 7.

Figure 5:
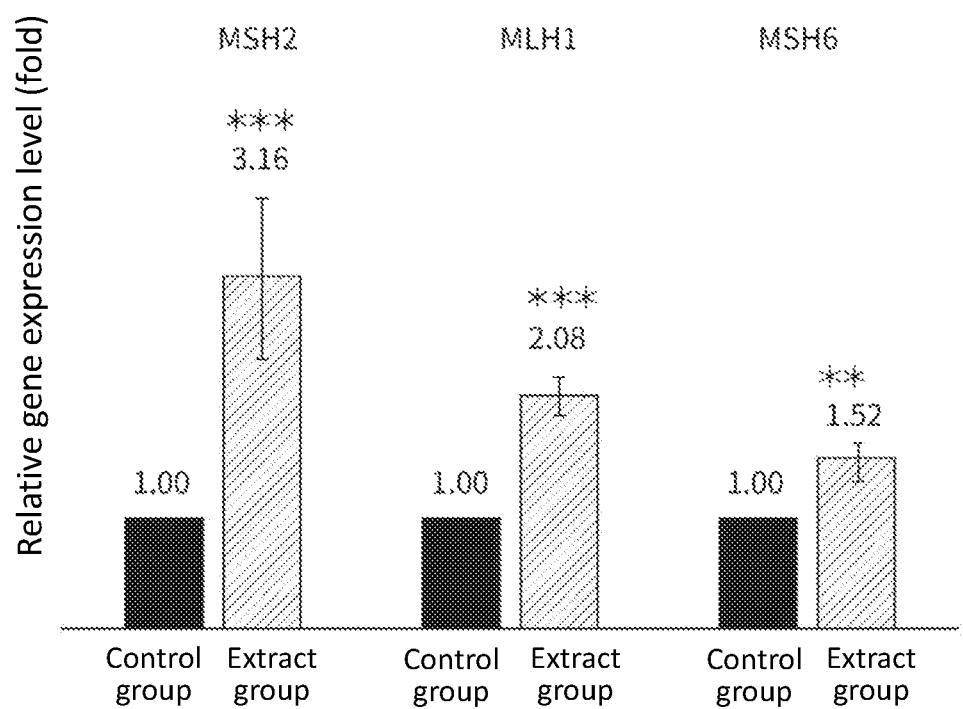
Figure 6:
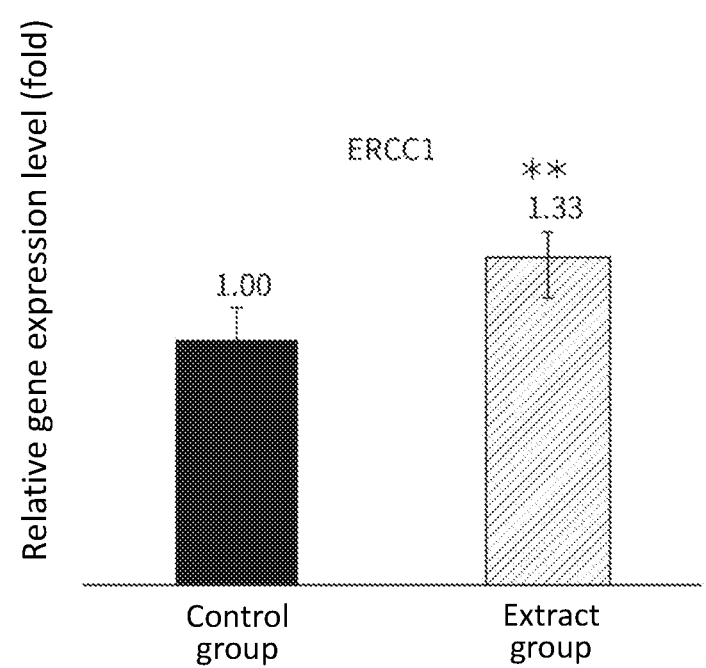
Figure 7:
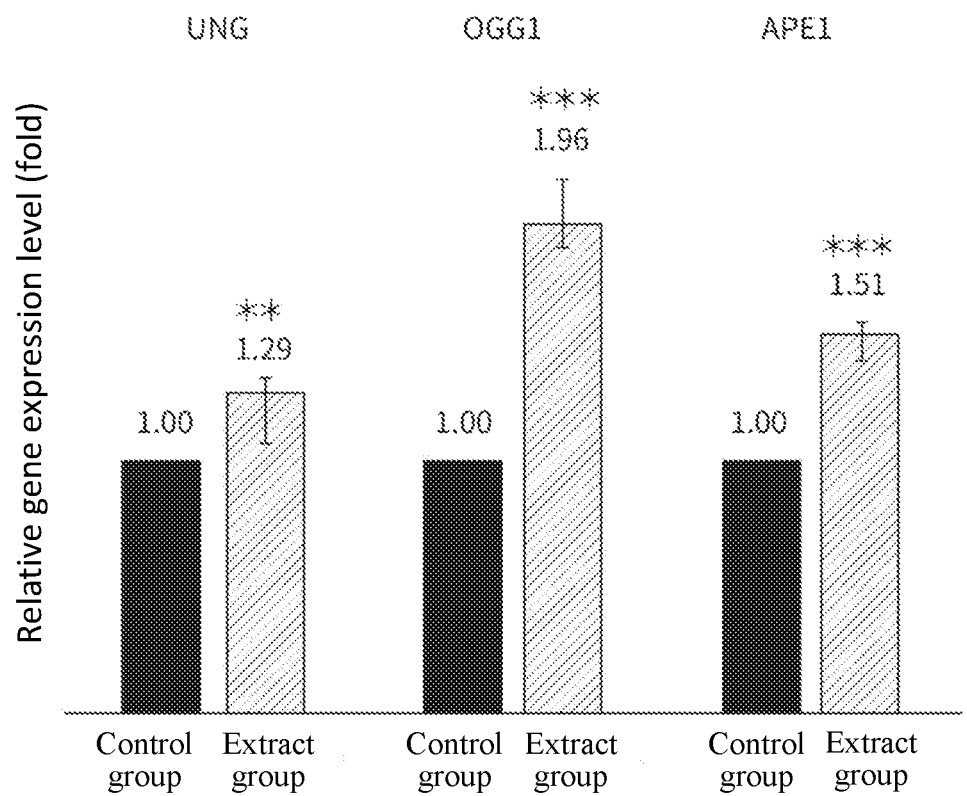

As shown in FIGS. 5 to 7, in comparison with the control group, the expression levels of MMR-related genes (including MSH2, MLH1 and MSH6), NER-related genes (including ERCC1), and BER-related genes (including UNG, OGG1 and APE1) of "Extract" group were all significantly increased. The results indicate that the orchid callus extract of the present invention can indeed increase the expression levels of DNA repair-related genes of skin cells, and thus, is effective in repairing damaged DNA in skin cells, thereby achieving the effects of delaying skin aging, repairing skin tissues, and/or preventing skin lesions.

As shown by the above Examples, the orchid callus extract provided in accordance with the present invention can indeed promote syntheses of collagen, elastin and hyaluronic acid in skin, enhance the antioxidant capability of skin cells, and assist in repairing damaged DNA in skin cells, and thus, is effective in moisturizing skin, increasing skin tenderness, increasing skin abundance, increasing skin elasticity, tightening skin, reducing skin textures, delaying skin aging, assisting in increasing content of collagen, repairing skin tissues, preventing skin lesions, and/or promoting wound healing.

What is claimed is:

1. A method for protecting skin, comprising administering to a subject in need an effective amount of an orchid callus extract, wherein the extract is a polar solvent extract of a callus of orchid leaves, and the orchid is *Phalaenopsis amabilis*.

2. The method as claimed in claim 1, wherein the polar solvent is selected from a group consisting of water, C1-C4 alcohols, and combinations thereof.

3. The method as claimed in claim 1, wherein the orchid callus extract is administered to the subject as a care product composition, a food product composition, or a pharmaceutical composition.

4. The method as claimed in claim 3, wherein the orchid callus extract is administered to the subject as a care product composition to moisturize skin, increase skin tenderness, increase skin abundance, increase skin elasticity, tighten skin, reduce skin textures, and/or delay skin aging.

5. The method as claimed in claim 4, wherein the care product composition is an essence, an emulsion, or a lotion.

6. The method as claimed in claim 3, wherein the orchid callus extract is administered to the subject as a food product composition to assist in increasing content of collagen.

7. The method as claimed in claim 6, wherein the collagen is type I collagen.

8. The method as claimed in claim 6, wherein the food product composition is a beauty beverage.

9. The method as claimed in claim 3, wherein the orchid callus extract is administered to the subject as a pharmaceutical composition to repair skin tissues, prevent skin lesions, and/or promote wound healing.

10. The method as claimed in claim 9, wherein the pharmaceutical composition is administered to the subject by transdermal administration, oral administration, subcutaneous injection, or a combination thereof.

\* \* \* \* \*